United States Patent
Ko

(10) Patent No.: US 11,833,361 B2
(45) Date of Patent: Dec. 5, 2023

(54) TREATMENT APPARATUS, METHOD OF CONTROLLING SAME AND THE TREATMENT METHOD

(71) Applicant: LUTRONIC CORPORATION, Goyang (KR)

(72) Inventor: Kwang Chon Ko, Paju (KR)

(73) Assignee: LUTRONIC CORPORATION, Goyang (KR)

( * ) Notice: Subject to any disclaimer, the term of this patent is extended or adjusted under 35 U.S.C. 154(b) by 1294 days.

(21) Appl. No.: 16/066,936

(22) PCT Filed: Jan. 3, 2018

(86) PCT No.: PCT/KR2018/000098
§ 371 (c)(1),
(2) Date: Jun. 28, 2018

(87) PCT Pub. No.: WO2018/128373
PCT Pub. Date: Jul. 12, 2018

(65) Prior Publication Data
US 2021/0196968 A1  Jul. 1, 2021

(30) Foreign Application Priority Data
Jan. 6, 2017 (KR) .................. 10-2017-0002535

(51) Int. Cl.
*A61N 1/40* (2006.01)
*A61B 18/14* (2006.01)
(Continued)

(52) U.S. Cl.
CPC .......... *A61N 1/403* (2013.01); *A61B 18/1477* (2013.01); *A61B 2018/00005* (2013.01);
(Continued)

(58) Field of Classification Search
CPC .......... A61N 1/403; A61B 2018/00005; A61B 2018/00011; A61B 2018/00017;
(Continued)

(56) References Cited

U.S. PATENT DOCUMENTS

2002/0151887 A1  10/2002 Stern et al.
2004/0181214 A1*  9/2004 Garabedian ........ A61B 18/1477
606/41
(Continued)

FOREIGN PATENT DOCUMENTS

JP  2006-513830 A  4/2006
JP  2009-544399 A  12/2009
(Continued)

*Primary Examiner* — Kaitlyn E Smith
*Assistant Examiner* — Bradford C. Blaise

(57) ABSTRACT

The present invention relates to a treatment apparatus including a housing, an insertion unit provided on one side of the housing and formed to be inserted into a tissue through a tissue surface, and a cooling unit cooling the one side of the insertion unit within the housing to prevent thermal damage to the tissue touched when the insertion unit heated during a treatment time is drawn out from or inserted into the tissue, and a method of controlling the same and a treatment method. According to the present invention have effects in that they can prevent a problem in that unnecessary damage to a tissue occurs while maintaining a treatment effect of the skin because the heated end of the insertion unit is cooled and moved.

13 Claims, 18 Drawing Sheets

(51) Int. Cl.
*A61B 18/02* (2006.01)
*A61B 18/00* (2006.01)

(52) U.S. Cl.
CPC ............... *A61B 2018/0016* (2013.01); *A61B 2018/0237* (2013.01); *A61B 2018/143* (2013.01); *A61B 2018/1425* (2013.01); *A61B 2018/1475* (2013.01)

(58) Field of Classification Search
CPC .. A61B 2018/0016; A61B 2018/00964; A61B 2018/0237; A61B 2018/0243; A61B 2018/025; A61B 2018/0256; A61B 2018/1425; A61B 2018/143; A61B 2018/1475; A61B 18/1477
See application file for complete search history.

(56) References Cited

U.S. PATENT DOCUMENTS

| | | | |
|---|---|---|---|
| 2005/0222565 A1* | 10/2005 | Manstein | A61M 5/158 606/41 |
| 2006/0129144 A1 | 6/2006 | Shin et al. | |
| 2007/0073285 A1* | 3/2007 | Peterson | A61B 18/1477 606/41 |
| 2008/0183251 A1 | 7/2008 | Azar et al. | |
| 2010/0010480 A1* | 1/2010 | Mehta | A61B 18/203 601/3 |
| 2010/0179531 A1* | 7/2010 | Nebrigic | A61B 18/14 606/33 |
| 2012/0158100 A1* | 6/2012 | Schomacker | A61B 18/1477 607/101 |
| 2014/0155963 A1* | 6/2014 | Ko | A61H 39/08 607/101 |
| 2014/0194789 A1* | 7/2014 | Ko | A61H 99/00 601/18 |
| 2014/0358200 A1* | 12/2014 | Ko | A61N 1/06 607/101 |

FOREIGN PATENT DOCUMENTS

| | | |
|---|---|---|
| KR | 10-0965564 B1 | 6/2010 |
| KR | 10-2011-0000790 A | 1/2011 |
| KR | 10-2013-0106015 A | 9/2013 |
| KR | 10-2015-0014441 A | 2/2015 |
| WO | 2013/164996 A1 | 11/2013 |

\* cited by examiner

TREATMENT APPARATUS, METHOD OF CONTROLLING SAME AND THE TREATMENT METHOD

CROSS-REFERENCE TO RELATED APPLICATIONS

The present specification is a U.S. National Stage of International Patent Application No. PCT/KR2018/000098, filed Jan. 3, 2018, which claims priority to and the benefit of Korean Patent Application No. 10-2017-0002535, filed in the Korean Intellectual Property Office on Jan. 6, 2017, the entire contents of which are incorporated herein by reference.

TECHNICAL FIELD

The present invention relates to a treatment apparatus and a method of controlling the same and the treatment method, more particularly, to a treatment apparatus into a tissue of the human body to perform treatment in an invasion manner and a method of controlling the same and a treatment method.

BACKGROUND ART

A method of treating a tissue may be divided into a method of treating a tissue outside the tissue and an invasive treatment method of treating a tissue by inserting some of or the entire treatment apparatus into the tissue. The invasive treatment method basically uses a treatment apparatus having a thin-necked insertion unit, such as a needle or a catheter. Treatment is performed after the treatment apparatus is inserted up to a target location within a tissue.

The invasive treatment method includes various treatment behaviors, such as delivering a treating substance to the inside of a tissue, performing surgical treatment through a mechanical operation in the state in which a specific tissue within a tissue is adjacent, or delivering energy to a target location within a tissue. The treatment method has been disclosed in Korean Patent Application Publication No. 10-2011-0000790, and is applied in various methods.

In general, the invasive treatment method has problems in that it may cause unnecessary damage to a touched tissue in a process of drawing out a heated needle during treatment and cause unnecessary damage in an insertion process when the needle is inserted into the tissue again.

DISCLOSURE

Technical Problem

An object of the present invention is to provide a treatment apparatus capable of preventing damage to a touched tissue due to a movement of a heated electrode when the treatment apparatus is inserted into the tissue and transfers energy in a conventional technology, and a method of controlling the same.

Technical Solution

As means for solving the problem, there may be provided a treatment apparatus, including a housing, an insertion unit provided on one side of the housing and formed to be inserted into a tissue through a tissue surface, and a cooling unit cooling a part of the insertion unit within the housing to prevent thermal damage to the tissue touched when the insertion unit heated during a treatment time is drawn out from or inserted into the tissue.

In this case, the treatment apparatus may further include a controller controlling energy applied to the insertion unit and controlling the cooling unit so that the insertion unit is cooled when energy is not applied to the insertion unit.

In this case, the controller may drive a driving unit supporting the insertion unit so that the insertion unit is selectively inserted into the tissue, may apply the energy in the state in which the insertion unit has been inserted into the tissue, and may control the driving of the cooling unit so that the driving includes an operation period in which the insertion unit is drawn out from the tissue.

Furthermore, the controller may control to stop the driving of the cooling unit when the end of the insertion unit is cooled to a specific temperature or less.

In this case, the specific temperature may be a temperature at which tissue coagulation or ablation does not occur.

Meanwhile, the insertion unit may be provided in a tip module detachably configured in the housing. An electrode may be provided toward the outward direction of the housing on one side of the tip module and the tip module may be supported by the driving unit in the inward direction of the housing. The cooling unit may be configured to cool the inward direction of the tip module.

Furthermore, the tip module may include a substrate to which the electrode may be fixed. The electrode may include a protruded part penetrating the substrate to protrude toward the inward direction of the housing in a specific length. The cooling unit may be configured to cool the protruded part.

In this case, the cooling unit may cool the insertion unit using forced convection.

Furthermore, the insertion unit may seal the inside and outside of the housing. The cooling unit may be configured to include a fan preventing the cooling of the tissue neighboring the insertion unit and cooling the one side of the insertion unit within the housing.

Meanwhile, the treatment apparatus may further include a cooling fin provided to come into contact with the protruded part to improve cooling efficiency of the electrode.

Moreover, the cooling unit may include a heat sink selectively coming into contact with the protruded part to perform cooling so that the electrode is cooled through conduction.

Furthermore, the cooling unit may include spray holes configured to spray a liquefied material onto the protruded part so that the protruded part is cooled by absorbing evaporation heat.

In this case, the liquefied material may include Cryozen.

Furthermore, wherein the electrode may include a plurality of micro needles and has a thickness of 200 μm or less.

Meanwhile, the energy may be RF energy.

Furthermore, the material of the electrode may include at least one of SUS304, gold, and titanium.

Additionally, there may be provided a method of controlling a treatment apparatus, comprising steps of advancing the insertion unit so that a part of the insertion unit into a tissue, applying RF energy, driving a cooling unit for cooling a part of the insertion unit so that prevent thermal damage to a tissue touched when the insertion unit is drawn out from the tissue; and drawing out the insertion unit and positioning the insertion unit at an original position.

In this case, the cooling step may be performed until a temperature of the inserted insertion unit is cooled to a specific temperature or less. The original positioning step may be performed after the insertion unit drops to the specific temperature.

Specifically, the insertion unit may include a tip module. The tip module may be configured to include a substrate and an electrode having a protruded part protruded at a specific length through the substrate. The cooling step may include cooling the protruded part.

Furthermore, the cooling step may include cooling the protruded part while preventing the cooling of the tissue surface.

Advantageous Effects

The treatment apparatus and the method of controlling the same according to the present invention have effects in that they can prevent a problem in that unnecessary damage to a tissue occurs while maintaining a treatment effect of the skin.

MODE FOR INVENTION

Figure 1:
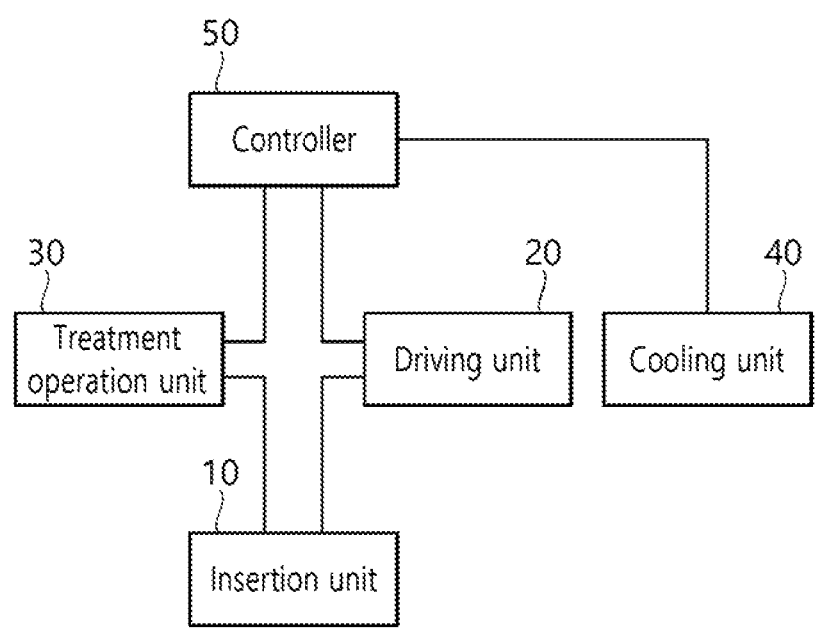
FIG. 1 is a block diagram showing the configuration of a treatment apparatus according to a first embodiment of the present invention.

Hereinafter, a treatment apparatus and a method of controlling the same according to embodiments of the present invention are described in detail with reference to the accompanying drawings. Furthermore, in the following description of the embodiments, elements may be named differently in the field to which the present invention pertains. However, if the elements have functional similarity and identity, they may be considered to be equivalent elements although they adopt modified embodiments. Furthermore, reference numerals assigned to respective elements are written for convenience of description. However, contents shown in the drawings in which the reference numerals are written do not restrict respective elements to the ranges in the drawings. Likewise, although the elements in the drawings adopt partially modified embodiments, they may be considered to be equivalent elements if the elements have functional similarity and identity. Furthermore, a description of an element is omitted if the element is recognized as being an element that must be naturally included in view of the level of a person having ordinary skill in the art.

Hereinafter, a "treatment apparatus" includes all apparatuses for treating mammals including people. The treatment apparatus may include may include various treatment apparatuses used to improve a lesion or the state of a tissue. For example, the treatment apparatus includes an apparatus transferring treating substances, such as medicines, anesthetic, and stem cells, an operation apparatus for surgically treating a specific tissue, and various treatment apparatuses transferring RF energy.

Hereinafter, a "tissue" means a set of cells forming various body organs of an animal including people, and includes various tissues forming various organs within the body, including a skin tissue.

Hereinafter, an "insertion unit" means an element that belongs to the treatment apparatus and that is inserted into a tissue. The insertion unit includes various structures, each one having a sharp, thin and lengthy end, such as a needle, micro needle or catheter, and being inserted up to a tissue through a surface of the tissue.

FIG. 1 is a block diagram showing the configuration of a treatment apparatus according to a first embodiment of the present invention.

FIG. 1 is a block diagram showing the configuration of a treatment apparatus according to a first embodiment of the present invention. As shown in FIG. 1, the treatment apparatus according to the present invention is configured to include an insertion unit 10 formed to be inserted into a tissue, a driving unit 20 driving the insertion unit 10, a treatment operation unit 30 for performing treatment on the inside of a tissue through the insertion unit 10, a cooling unit 40, and a controller 50 controlling the operations of various elements including the driving unit and the treatment unit.

The insertion unit 10 is an element inserted up to the inside of a tissue through a tissue surface as described above. The insertion unit 10 has a lengthy structure having a sharp end and a small diameter so that it can be easily inserted into a tissue. In the present embodiment, the insertion unit 10 includes a plurality of needles, but may have various structures, such as a singular needle structure or catheter. Furthermore, a cooling fin or a protrusion protruded to a specific length in such a way as to perform the same function as the cooling fin may be provided one side of the insertion unit 10 so that heat dissipation is easily performed. The insertion unit 10 further includes an element necessary for the execution of treatment depending on a treatment method of the treatment apparatus. For example, in the case of a treatment apparatus that performs treatment using a method of transferring a treatment substance, the insertion unit may include a channel for injecting a treatment substance therein. Alternatively, in the case of a treatment apparatus that performs treatment using a method of transferring RF energy to the inside of a tissue, the insertion unit may include an electrode 11 for transferring RF energy. The insertion unit 10 is positioned in a handpiece, and may be configured to pop in and out the end of the handpiece and inserted into a tissue.

The driving unit 20 is an element that linearly moves the insertion unit 10 so that the insertion unit advances and retracts. The insertion unit 10 performs an operation of being inserted into a tissue or drawn out from a tissue by the driving of the driving unit 20. For example, the driving unit 20 may be configured using an actuator or may be configured using various driving members.

The treatment operation unit 30 is an element operating for the execution of treatment. The location where treatment is actually performed is the end of the insertion unit 10 positioned within a tissue. The treatment operation unit 30 performs an operation for treatment at the end of the insertion unit 10. For example, the treatment operation unit may have a pump or valve for transferring a treatment substance from a treatment substance accommodation unit (not shown) to the end of the insertion unit 10. For another example, the treatment operation unit may be an RF generator for supplying RF energy to the end of the insertion unit 10. In addition, the treatment operation unit may have various elements depending on a treatment method of the treatment apparatus.

The cooling unit 40 is configured to cool the heated end of the insertion unit 10 when the end of the insertion unit 10 applies energy. The insertion unit 10 is inserted into a tissue to perform treatment, and enters the tissue through a surface for the treatment. In this case, a path from the surface to a target volume is an insertion path into which the end of the insertion unit 10 is inserted. When treatment for a corresponding portion is terminated, an operation of drawing out the end of the insertion unit 10 from the tissue is performed. At this time, since the end of the insertion unit 10 has been heated, damage to the tissue attributable to high heat may occur at a touched portion on the insertion path when the operation of drawing out the end of the insertion unit 10 is performed. Such damage may intensively occur in the tissue locally coming into contact with the end of the insertion unit 10. Unnecessary damage to the tissue can be minimized by cooling the end of the insertion unit 10 through the cooling unit 40 before the process of drawing out the end of the insertion unit 10 from the tissue or during the process. The cooling unit 40 indirectly cools the end of the insertion unit 10 inserted into the tissue by cooling one side of the insertion unit 10 without directly cooling the end of the insertion unit 10. The cooling unit 40 cools one side of the insertion unit 10, and thus heat transfer is performed from the end of the insertion unit 10 to one side of the insertion unit 10, thereby being capable of finally cooling the end of the insertion unit 10. The cooling unit 40 may be configured to perform cooling in an air cooling type or a water cooling type. Meanwhile, while the end of the insertion unit 10 is cooled, the cooling may be performed within the insertion unit 10 so that a tissue surface is not affected.

The controller 60 controls the operations of various elements of the treatment apparatus, including the driving unit 20, the treatment operation unit 30, and the cooling unit 40. The controller 60 may perform treatment by driving the elements based on a user's control or a preset mode. The controller may further include a separate database or processor. Accordingly, when a variety of types of information necessary for control is transmitted to the controller, the controller may derive a proper control signal using previously stored data or a calculation method based on such information. Specifically, the controller may control the driving unit, the treatment operation unit, and the cooling unit 40 by associating them so that the cooling unit 40 is driven after the insertion unit 10 performs treatment. In this case, the control of the cooling unit 40 includes open loop control of driving the cooling unit 40 for a specific time and feedback control using a measured value of the temperature of the end of the insertion unit 10 or one side of the insertion unit 10 using a temperature sensor. Meanwhile, the specific time may be set by incorporating a previously stored temperature distribution according to the heating of the insertion unit 10 and a temperature change according to cooling. In this case, a reference temperature may be a temperature at which a tissue is not coagulated or ablated by the end of the insertion unit 10. Specifically, the reference temperature may be about 70 degrees Celsius. This is only an example, and the controller may operate so that cooling is performed based on various temperatures depending on a treatment object.

Figure 2A:
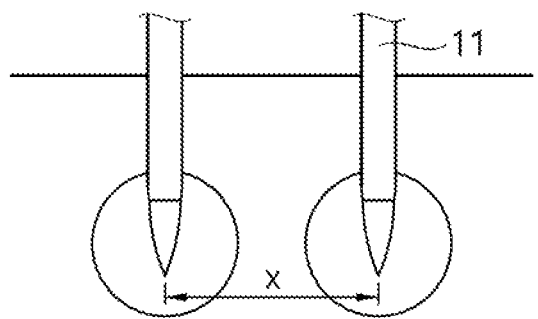
FIGS. 2a, 2b and 2c are the conceptual diagram of a tissue, a graph and diagram showing a temperature distribution when treatment using electrodes is performed.
Figure 2B:
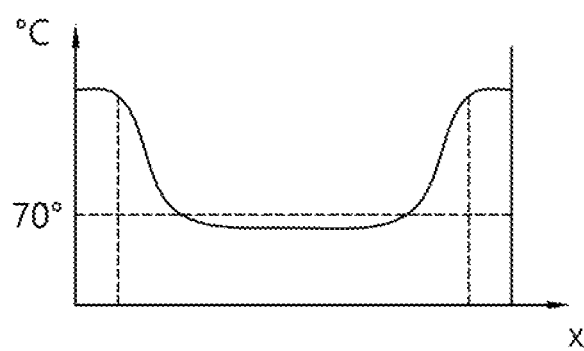
Figure 2C:
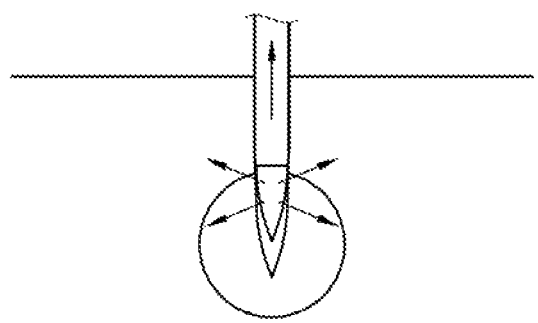

FIGS. 2*a*, 2*b* and 2*c* are the conceptual diagram of a tissue, a graph and diagram showing a temperature distribution when treatment using the electrodes 11 is performed. The drawing shows an example in which treatment is performed by inserting the electrode 11 of a bipolar type into the tissue and applying RF energy. As shown in FIG. 2*a*, treatment is performed between two electrodes 11. As shown in FIG. 2*b*, after energy is applied for a specific time, a temperature distribution appears from the middle portion of both the electrodes 11 horizontally. The drawing shows an example in which as the energy is applied, both the electrodes 11 are heated at the highest temperature and a surrounding tissue becomes about 70 degrees Celsius, so treatment is performed, but this is only an example, the temperature may be determined based on various elements, such as the characteristics of a tissue, applied energy, and an application time.

As in FIG. 2*c*, when the electrode 11 is drawn out from the tissue after the energy is applied, unnecessary damage to the tissue coming into contact with the electrode 11 occurs due to energy remaining within the electrode 11. Furthermore, although not shown, if the electrode 11 has been excessively heated, a touched tissue may be thermally damaged when the electrode 11 is inserted into the tissue in a next cycle in addition to when the electrode is drawn out from the tissue.

Figure 3:
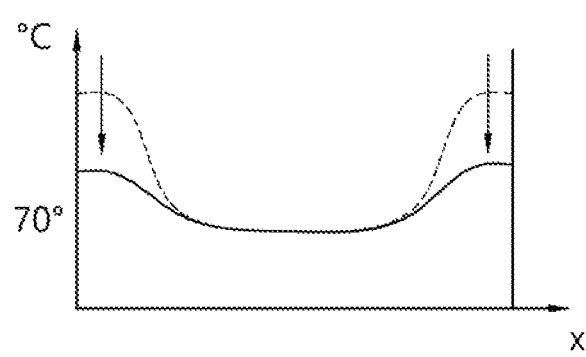
FIG. 3 is a graph showing a temperature distribution before and after cooling when treatment using a first embodiment is performed.

FIG. 3 is a graph showing a temperature distribution before and after cooling when treatment using a first embodiment is performed. As described above, heat energy can be lowered by cooling the electrode 11 before the electrode 11 is drawn out from a tissue after energy is applied. In this case, the electrode 11 has very high thermal conductivity because it may be made of a metallic material, so a temperature change in the tissue is very small and heat energy remaining within the electrode 11 can be discharged. Accordingly, thermal damage to a tissue touched in a process of drawing out the electrode from the tissue can be prevented.

Hereinafter, a treatment apparatus of a second embodiment is described with reference to FIGS. 4 to 7.

Figure 4:
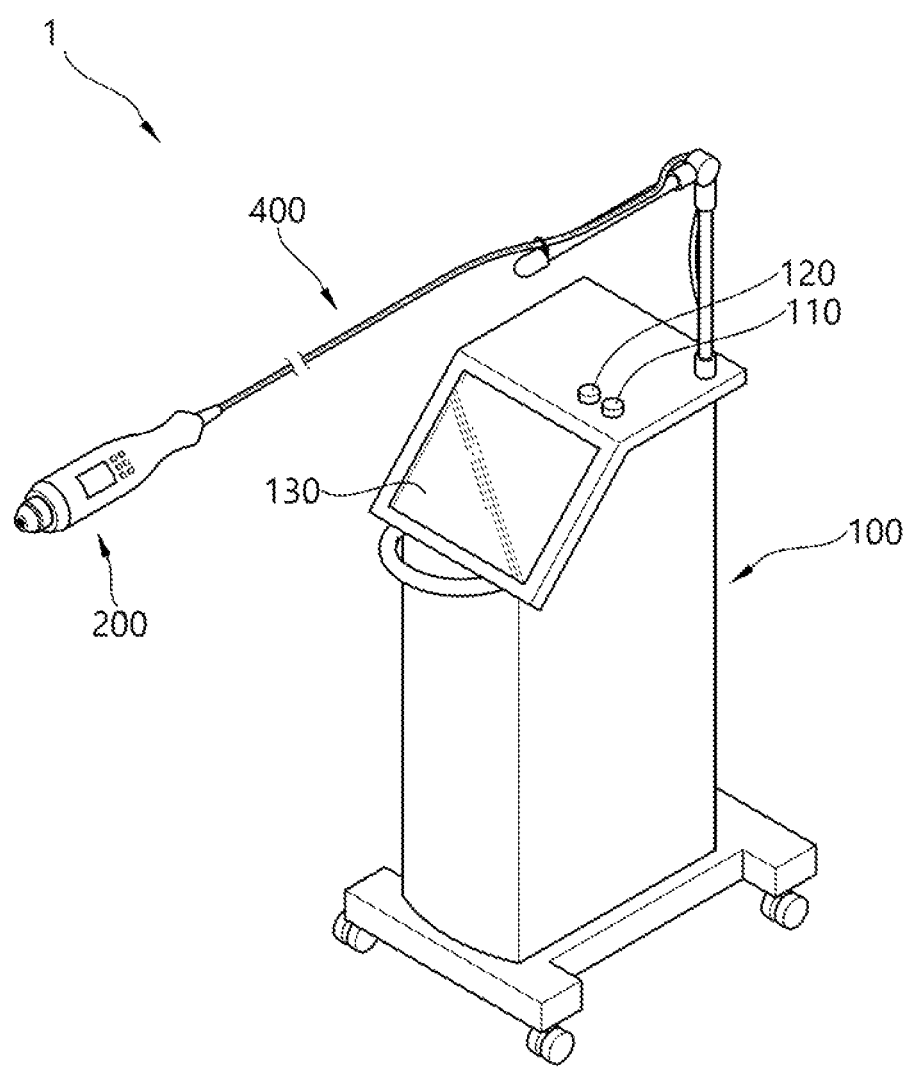
FIG. 4 is a perspective view of a second embodiment.
Figure 5:
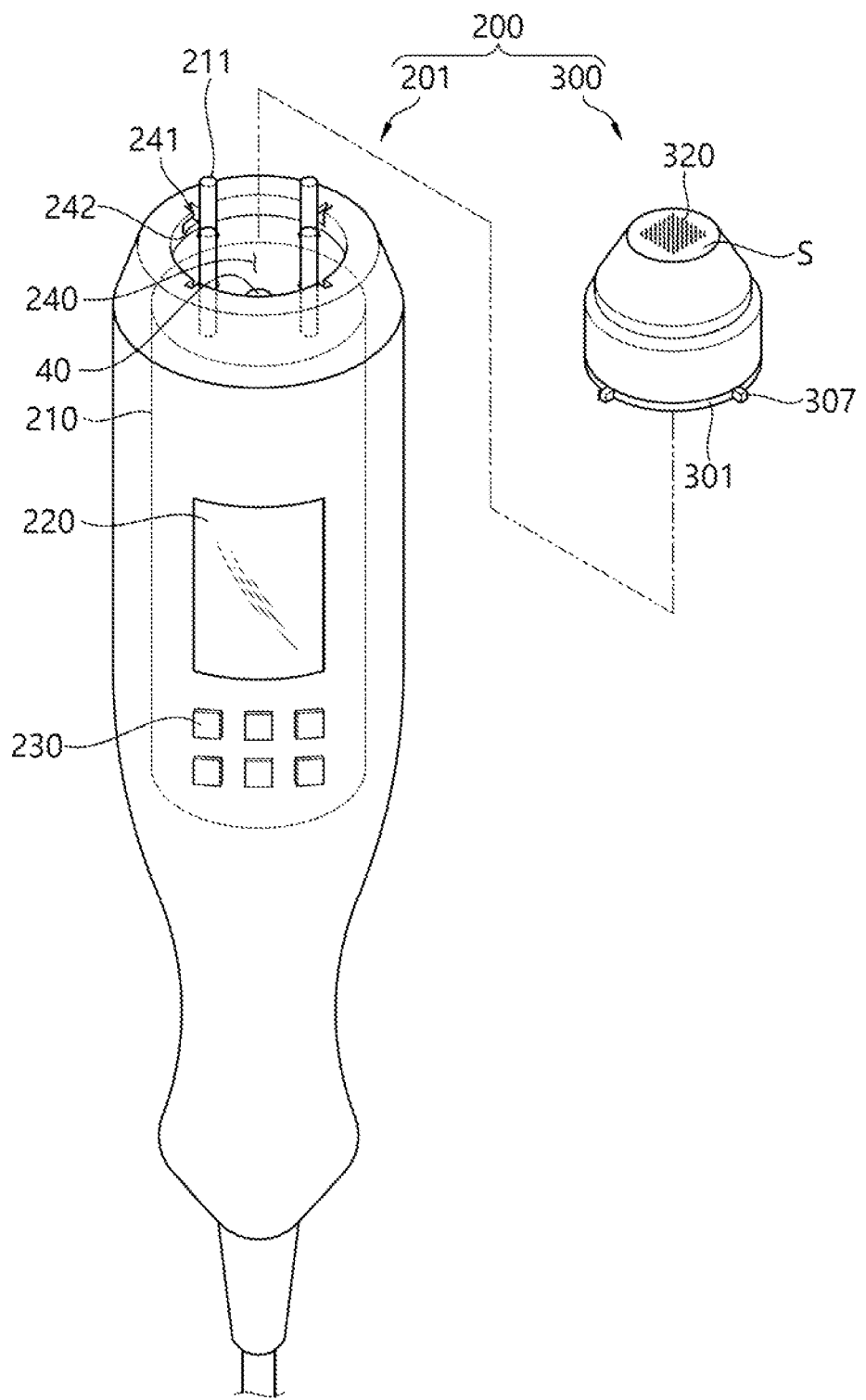
FIG. 5 is an enlarged diagram of a handpiece of FIG. 3.
Figure 6:
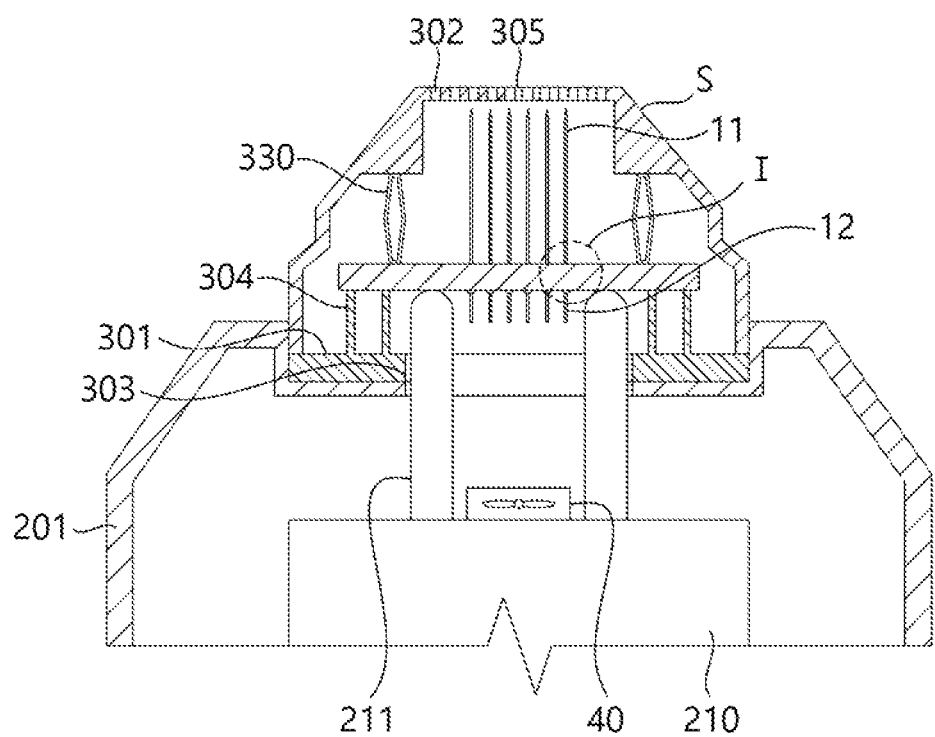
FIG. 6 is a cross-sectional view of the end of the handpiece.

FIG. 4 is a perspective view of the second embodiment, and FIG. 5 is an enlarged diagram of a handpiece of FIG. 3. The treatment apparatus 1 according to the present invention is an apparatus in which the insertion unit 10 is inserted into a skin tissue of the human body and transfers energy to the inside of the skin tissue. The insertion unit 10 of the present embodiment includes a plurality of needles, and may transfer energy to the inside of a skin tissue through the ends of the needles. Referring to FIGS. 5 and 6, the treatment apparatus according to the present invention includes a main body 100, a handpiece 200 enabling a user to perform treatment while the user graphs the handpiece, and a connection unit 400 connecting the main body and the handpiece.

An RF generator (not shown) may be provided within the main body 100. The RF generator is an element corresponding to the treatment operation unit (refer to 30 of FIG. 1) of the aforementioned embodiment, and generates RF energy used for treatment. The frequency of the RF energy generated by the RF generator may be controlled depending on the physical constitution, treatment purpose, a treatment portion, etc., of a patient. For example, RF energy used for skin treatment may be adjusted in the range of 0.1 to 0.8 MHz.

A power on/off switch 110, a frequency control lever 120 capable of controlling the frequency of RF energy generated by the RF generator, and a touch screen 130 displaying a variety of types of information including the operating contents of the treatment apparatus, enabling a user to input a command, and displaying treatment information may be positioned on an external surface of the main body 100.

Meanwhile, the handpiece 200 is connected to the main body by the connection unit 400. The connection unit 400 may transfer RF energy generated by the RF generator of the main body to a plurality of needles 320 corresponding to the insertion unit of the aforementioned embodiment, and may transfer power from the main body, which is necessary for various elements on the handpiece side to operate. The connection unit 400 is configured in a cable form, and may use a cable including a plurality of conducting wires whose metal lines are surrounded by insulating coating.

A driving unit 210 and the cooling unit 40 are positioned within the housing of the handpiece 200. The driving unit 210 is configured to linearly move output terminals 211 provided at the end of the driving unit in the length direction. When the output terminals 211 linearly move, the plurality of needles 320 disposed at the ends of the output terminals may pop in and out to the outside of the contact surface of the handpiece. Accordingly, the plurality of needles 320 may be inserted into a tissue of a patient or drawn out from the tissue by the driving of the driving unit 210. The driving unit 210 may consist of a solenoid, a linear actuator using a hydraulic/pneumatic cylinder, etc. The cooling unit 40 consists of a fan and may be configured to generate cool air toward a tip module to be described later, which is provided at the end of the handpiece. In this case, a single cooling unit 40 has been illustrated, but may be configured in plural, and the position where the cooling unit is installed is not limited to the illustrated position.

A handpiece manipulation unit 230 and a handpiece display unit 220 may be provided on an external surface of the handpiece 200. The handpiece manipulation unit 230 is configured to manipulate the on/off of the handpiece, control the insertion depth of the insertion unit 10, or control the amount of energy transferred through the insertion unit 10. The handpiece display unit 220 may display a variety of types of information necessary in a set mode or during treatment with respect to a user. Accordingly, in the state in which the user has graphed the handpiece, the user can easily manipulate treatment contents during treatment through the handpiece manipulation unit 230, and can easily check treatment contents through the handpiece display unit 220.

A tip module 300 is provided at the end of the handpiece. The tip module includes the plurality of needles and may be detachably positioned at the main body 201 of the handpiece. Specifically, a base 301 forms the bottom of the tip module, and outward protruded detachment protrusions 307 are formed at the outer wall of the base. A hollow through which cool air from the cooling unit 40 can pass may be formed at a portion that belongs to the base 301 and that neighbors the protruded parts of the needles. Furthermore, a plurality of through holes through which cool air can be discharged may be formed in an outer part not neighboring the protruded parts of the needles. Guide grooves 241 that guide the detachment protrusions and an anti-separation groove 242 for preventing the detachment protrusions 307 guided along the guide grooves 241 from being separated are formed in a recess unit 240 to which the tip module is coupled on the handpiece side. Furthermore, the detachment protrusions 307 of the tip module are disposed at the handpiece in such manner that they are guided along the guide grooves 241 and coupled to the anti-separation groove 242. Meanwhile, the tip module may be configured to seal the inside and outside of the handpiece in such a manner that it cools the needles 320 therein by the driving of the cooling unit 40, but prevents cool air from affecting a skin surface due to its outward flow. In this case, the sealing means that a gap is formed between the tip module and the handpiece to the extent that a skin surface is not affected by the outward flow of the cool air.

In this case, an example in which the tip module is detachably positioned at the handpiece as in the present embodiment is illustrative, and the tip module may be integrated with the handpiece.

Figure 7:
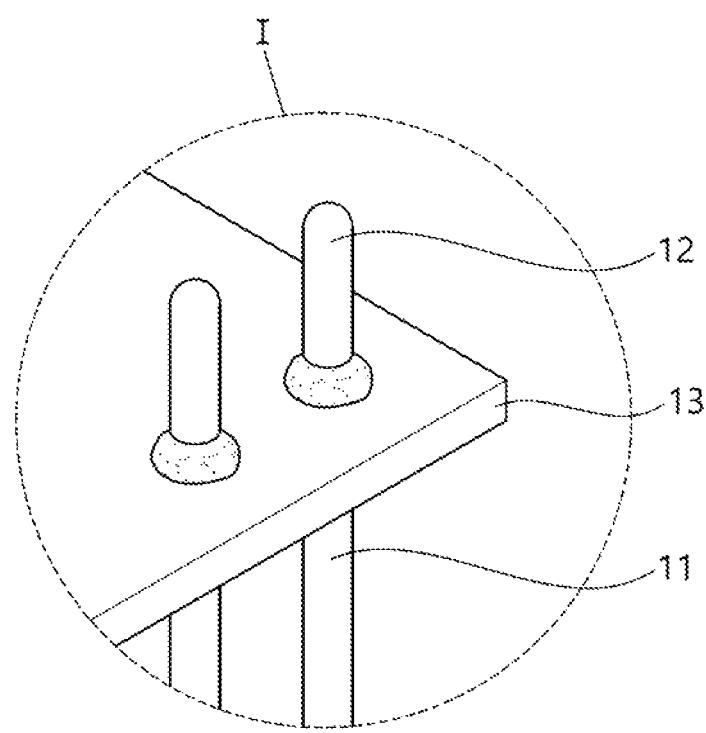
FIG. 7 is an enlarged view of part of an electrode and protrusion.

FIG. 6 is a cross-sectional view of the end of the handpiece, and FIG. 7 is an enlarged view of part of a portion I of FIG. 6, that is, the electrode 11 and the protruded part 12. Referring to FIG. 6, the end of the handpiece 200 is a portion that comes into contact with a skin tissue and where treatment is performed. A substrate 13 in which a plurality of the electrodes 11 is disposed is provided within the tip module. The plurality of needles is fixed and disposed in the substrate 13 in a matrix form. RF energy is transferred to the needles through a circuit formed in the substrate 13. Meanwhile, the plurality of needle-shaped electrodes 11 is collectively called the "electrode 11" hereunder. In this case, the electrode 11 is fixed to the substrate 13 so that the protruded part 12 of the electrode 11 protruded toward the inward direction of the handpiece in a specific length through the substrate 13 is formed. Accordingly, when the protruded part 12 is cooled, heat energy generated at the end of the electrode 11 can be efficiently discharged through the protruded part 12 by thermal conduction. The protruded part 12 has been illustrated as being formed in the same cross-sectional shape as the electrode 11, but may be applied in various manners, such as a cooling fin form, so that cooling efficiency by cool air is applied. Meanwhile, the material of the electrode 11 may be a material having excellent thermal conductivity, and may be made of gold, SUS304 or titanium.

Specifically, the electrode 11 may include a micro electrode 11 having a diameter of approximately 5 to 500 μm. The electrode 11 is made of a conductive material so that it can transfer RF energy. A portion belonging to a surface of each electrode 11 other than the tip is made of an insulating material 321 so that it cannot transfer RF energy to a tissue. Accordingly, part of the tip of each needle is configured to function as the electrode 11 and to transfer RF energy to a tissue. Accordingly, RF energy can be selectively transferred to the portion where the end of the electrode 11 is positioned during treatment.

The front S of the tip module may form a portion that neighbors or comes into contact with the skin of a patient upon treatment. A plurality of through holes 302 through which the plurality of electrodes 11 pops in and out may be formed in the front of the tip module.

At least one hole 303 through which the output terminal 211 can pass is provided at the bottom of the tip module. The output terminal 211 linearly moves along the hole 303 and pressurizes the substrate 13 when the driving unit 210 operates. The back of the substrate 13 is seated in a support 304 within the tip module. The front of the substrate 13 is pressurized by an elastic member 330 positioned within the tip module. When the output terminal 211 moves to pressurize the substrate 13, the substrate 13 is separated from the support 304 and advances, and the plurality of electrodes 11 is protruded toward the front of the through hole 302 and inserted into a skin tissue. Furthermore, when the output terminal 211 retracts by the driving of the driving unit 210, the substrate 13 retracts by the restoring force of the elastic member 330 and thus the plurality of electrodes 11 returns to the inside of the tip module. Although not separately shown, a separate guide member for guiding the path along which the aforementioned support plate moves may be further provided.

Although not shown in the drawing specifically, the circuit of the substrate 13 may be configured to be electrically connected to the RF generator of the main body when the tip module is positioned in the handpiece. Alternatively, the circuit of the support plate may be configured to be selectively electrically connected to the RF generator when the substrate is pressurized by the output terminal 211 (e.g., the electrode 11 is formed at the end of the output terminal and electrically connected to the support plate upon pressurization).

Hereinafter, an operation of the present embodiment is described in detail with reference to FIG. 8.

Figure 8A:
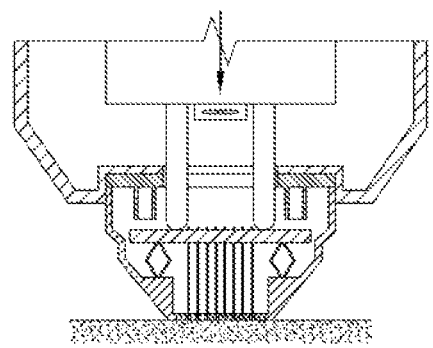
FIGS. 8a, 8b, 8c and 8d show the state in which the second embodiment operates.
Figure 8B:
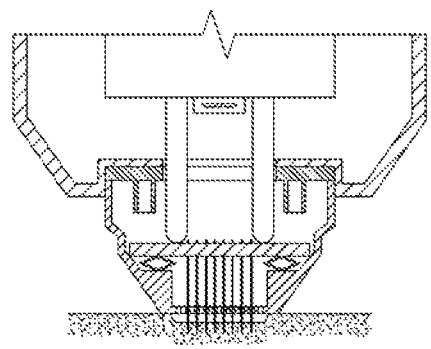
Figure 8C:
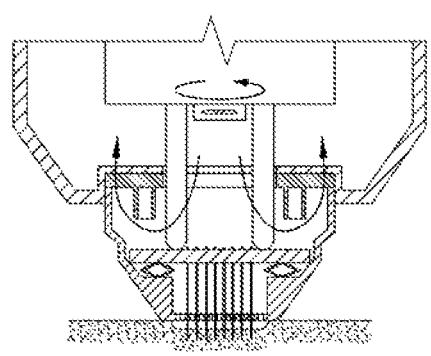
Figure 8D:
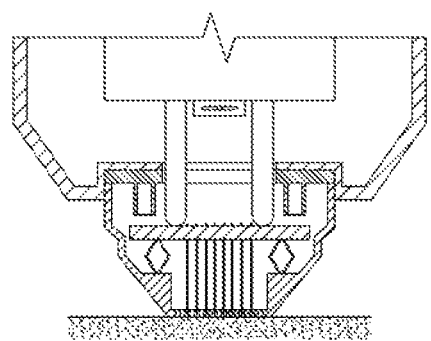

FIGS. 8a, 8b, 8c and 8d show the state in which the second embodiment operates. As shown in FIG. 8a, upon treatment, the end (the end where the electrode 11 is provided) of the handpiece is downward positioned to neighbor a skin tissue T. Thereafter, the driving unit supports the substrate 13 and thus the electrode 11 is inserted into the tissue (FIG. 8b). After the insertion, energy is applied to heat the inside of the tissue, so treatment is performed. After the application of the energy is stopped, cool air is insufflated into the protruded part using forced convection, that is, by driving the cooling unit 40 (FIG. 8c). When the temperature of the protruded part drops by driving the cooling unit 40 for a specific time, a temperature at the end of the electrode 11 also drops. Thereafter, when the driving force of the driving unit is released, the electrode 11 is drawn out from the tissue by the restoring force of the elastic member 330. At this time, since the temperature at the end of the electrode 11 has sufficiently dropped, damage to the tissue touched while the end of the electrode 11 moves can be minimized (FIG. 8d).

Meanwhile, although not shown, the cooling unit 40 may continue to be driven to perform cooling during the period in which the operation of drawing out the insertion unit from the tissue is performed.

Hereinafter, a modified example of the cooling unit 40 is described in detail with reference to FIGS. 9 and 10.

Figure 9A:
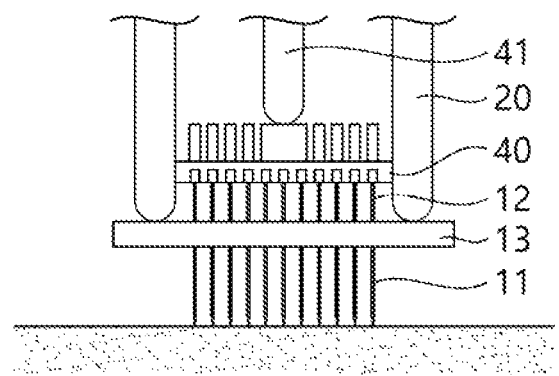
FIGS. 9a, 9b and 9c show the state in which a third embodiment operates.
Figure 9B:
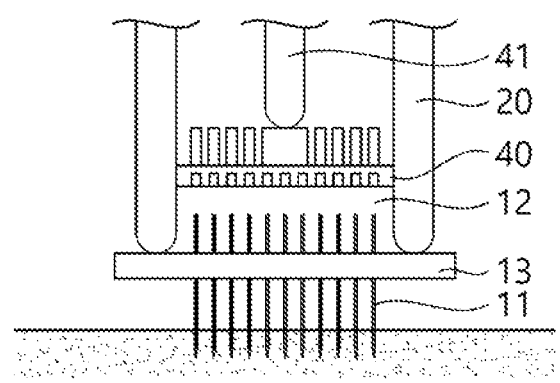
Figure 9C:
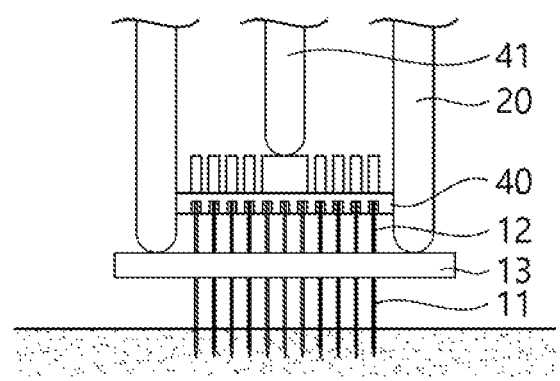

FIGS. 9a, 9b and 9c show the state in which a third embodiment operates. As shown, in the present embodiment, the cooling unit 40 may be configured to include a heat sink and a cooling driving unit. The cooling unit 40 is configured to selectively come into contact with the protruded part of the electrode 11 so that heat energy from the electrode 11 is conducted. A cooling fin is configured on one side of the heat sink so that the heat sink continues to discharge heat energy. The other side of the heat sink is configured to selectively come into contact with the protruded part of the electrode 11 and to absorb heat energy.

An operation is described. As in the previous embodiment, in the present embodiment, the handpiece is positioned in a tissue surface (FIG. 9a). After the electrode 11 is inserted by driving the driving unit, treatment is performed on the tissue by supplying energy (FIG. 9b). When the application of the energy to the electrode 11 is stopped, the cooling driving unit brings the heat sink to come into contact with the protruded part by moving the heat sink toward the electrode 11 in the state in which the electrode 11 has been inserted into the tissue so that the heated electrode 11 is cooled (FIG. 9c). In this case, the cooling driving unit 41 may be provided to support and move the heat sink. Furthermore, in order to improve heat transfer efficiency by increasing a contact surface area between the plurality of protruded parts and the heat sink, a plurality of accommodation protrusion grooves may be provided at positions of one surface corresponding to the array of the protruded parts so that part of each of the protruded parts is inserted. In this case, the heat sink may discharge heat energy into the air by natural convection, and may include a separate fan for supplying cool air toward the cooling fin of the heat sink.

Figure 10:
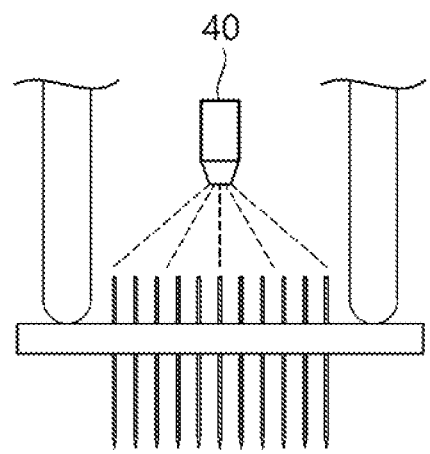
FIG. 10 is a cross-sectional view of the tip of the handpiece of a fourth embodiment.

FIG. 10 is a cross-sectional view of the tip of the handpiece of a fourth embodiment. The same elements as those of the previous embodiment have been omitted, and elements are indicated in brief for description. As shown, the present embodiment shows a configuration in which the cooling unit 40 cools the electrode 11 in the water cooling type. In this case, the water cooling type uses a material of a liquid state and refers to a cooling method using evaporation heat.

As shown, the cooling unit 40 may be configured to include spray holes capable of spraying a liquefied material toward the protruded parts. The spray hole has a nozzle formed on the side of the electrode 11 and may be configured in a proper spray range so that the liquefied material is spread on to the entire matrix of the electrode 11. The liquefied material that is sprayed and comes into contact with the protruded parts is evaporated by heat energy from the protruded part. At this time, the protruded part may be cooled faster compared to the aforementioned embodiment. Meanwhile, the amount of the liquefied material sprayed once may be determined by taking into consideration the amount of heat energy that must be lost in order to lower the protruded part to a reference temperature by considering the heat capacity of the matrix of the electrodes 11 and evaporation heat of the liquefied material. If the protruded part is to drop to the reference temperature so that electrical interference attributable to the liquefied material is removed when a next-time treatment cycle is performed, the amount of the liquefied material may be determined to be the amount that the entire applied liquefied material can be evaporated.

A material having a boiling point lower than the reference temperature may be selected as the liquefied material sop that the protruded part rapidly drops to the reference temperature. In this case, various materials may be selected by taking into consideration evaporation heat and the boiling point. For example, Cryozen may be selected and applied as the liquefied material.

Figure 11:
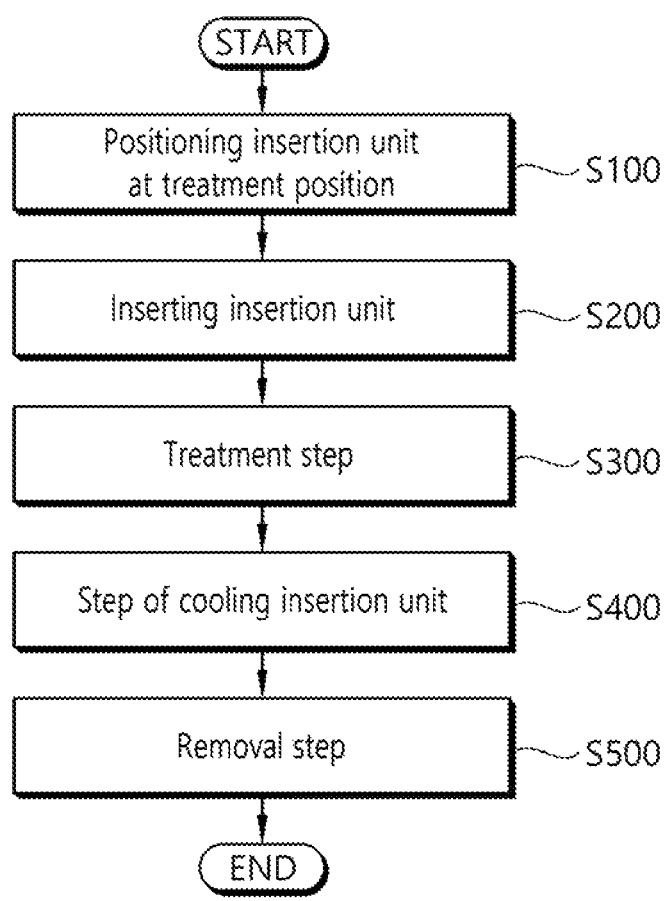
FIG. 11 is a flowchart of a method of controlling the treatment apparatus according to a fifth embodiment of the present invention.

FIG. 11 is a flowchart of a method of controlling the treatment apparatus according to a fifth embodiment of the present invention.

As shown, the fifth embodiment according to the present invention is a method of controlling the treatment apparatus, and may be configured to include the step S100 of positioning the insertion unit at a treatment position, the step S200 of inserting the insertion unit into a tissue, the step S300 of applying RF energy, the step S400 of cooling the insertion unit, and a removal step S500.

The step S100 of positioning the insertion unit at a treatment position corresponds to the step of positioning the insertion unit on a surface of a tissue for treatment. The handpiece or independently configured insertion units are brought into contact with a tissue surface and fixed thereto. The step of positioning the insertion unit at a treatment position may be configured in a one-time manner and may correspond to a case where multiple points may be touched once when the multiple points are treated in order to treat a wide tissue.

The step S200 of inserting the insertion unit into the tissue corresponds to the step of inserting the end of the insertion unit up to the depth where the target tissue is positioned using the driving unit.

The step S300 of applying RF energy corresponds to the step of heating and treating the target tissue by applying RF energy to the target tissue through the insertion unit.

The step S400 of cooling the insertion unit corresponds to the step of cooling one side of the insertion unit, that is, part of the insertion unit that has not been inserted. The step corresponds to the step of cooling one side of the insertion unit to cool the end of the insertion unit inserted into the tissue. In this case, the step corresponds to the step of discharging unnecessary heat energy remained in the insertion unit after the application of the energy is terminated. The step of cooling the insertion unit may be performed in the air cooling type or the water cooling type. The step of cooling the insertion unit may be performed until the end of the insertion unit drops to a specific temperature or less. In this case, a temperature at the end of the insertion unit may be estimated from a temperature on one side of the insertion unit based on a temperature distribution from one side of the insertion unit to the end thereof. In this case, if the insertion unit includes the tip module including the needles, the step of cooling the insertion unit may be performed by cooling parts of the needles that have not been inserted. For example, the needle includes a protruded part protruded toward the side opposite the side where the needle is inserted with respect to the substrate to which the needle is fixed. The inserted needle can be finally cooled by cooling the protruded part. As in the aforementioned embodiment, in this case, the cooling may be performed on the inside of the housing of the handpiece so that only the needle is cooled while preventing the cooling of the tissue surface.

The removal step S500 corresponds to the step of drawing out the end of the insertion unit from the tissue and positioning it at the original position when the end of the insertion unit is cooled to a specific temperature or less.

Meanwhile, the removal step S500 may be performed after the step S400 of cooling the insertion unit or may be performed simultaneously with the step S400 of cooling the insertion unit. A treatment area ranges from the position into which the end of the insertion unit has been inserted to a specific distance toward the upper side. Cooling may not be meaningful because a tissue has already been denaturized in the treatment area. Accordingly, the insertion unit may be cooled at the same time while it is detached from the treatment area and the insertion unit may be cooled by the cooling unit when the end of the insertion unit passes through a portion other than the treatment area, thereby being capable of preventing damage. In this case, the time taken for one-cycle treatment can be reduced because the time taken for cooling can be reduced.

Treatment may be performed on a wide treatment area by repeatedly performing the step S100 of positioning the insertion unit at the treatment position to the removal step S500 while changing the treatment position.

The treatment apparatus and the method of controlling the same according to the present invention have effects in that they can prevent a problem in that unnecessary damage to a tissue occurs while maintaining a treatment effect of the skin because the heated end of the insertion unit is cooled and moved.

The invention claimed is:

1. A treatment apparatus, comprising:
a handpiece;
a tip module provided at an end of the handpiece, the tip module including an inner part in which micro needles and a substrate are disposed and a wall sealing the inner part, the micro needles being fixed to the substrate, the wall having at least one hole;
a driving unit disposed on an end portion of the handpiece, the driving unit including an output terminal that moves along the at least one hole and pressurizes the substrate when the driving unit operates; and
a cooling unit having a fan that supplies cooling air towards the inner part of the tip module through the at least one hole, thereby cooling all micro needles together,
wherein each of the micro needles comprises a first part and a second part, the second part being a protruded part penetrating the substrate to extend towards the handpiece in a specific length, the first part and the second part being included in a single body of each of the micro needles,
wherein the first part of each of the micro needles is configured to be inserted into a target tissue, so that energy is applied to the micro needles, the second part being positioned opposite to the first part of each of the micro needles with respect to the substrate,
wherein the cooling unit is configured to directly cool the second parts of the micro needles respectively without directly cooling a surface of the target tissue, after ending the applying of the energy,
wherein the specific length is shorter than a length of the first part of each of the micro needles, and
wherein the cooling unit is disposed between the driving unit and the wall of the tip module.

2. The treatment apparatus of claim 1, further comprising a controller configured to control the energy applied to the micro needles and control the cooling unit so that the micro needles are cooled when the energy is not applied to the micro needles.

3. The treatment apparatus of claim 2,
wherein the controller is configured to:
drive the driving unit supporting the substrate so that the micro needles are selectively inserted into the target tissue,
apply the energy when the micro needles have been inserted into the target tissue, and
control the cooling unit so that the cooling unit operates for a period of time including a time during which the micro needles are retrieved from the target tissue.

4. The treatment apparatus of claim 3, wherein the controller is configured to stop the operation of the cooling unit when the micro needles are cooled to a specific temperature or less.

5. The treatment apparatus of claim 4, wherein the specific temperature is a temperature at which tissue coagulation or ablation does not occur.

6. The treatment apparatus of claim 3,
wherein the tip module is configured to be detachable from the handpiece, and
wherein the cooling unit is configured to cool the inner part of the tip module in which the second parts are positioned.

7. The treatment apparatus of claim 1, wherein the cooling unit is configured to cool the second parts of the micro needles using forced convection.

8. The treatment apparatus of claim 7, wherein:
the tip module is configured to seal the handpiece when engaged with the handpiece.

9. The treatment apparatus of claim 1, wherein each of the micro needles has a thickness of 200 µm or less.

10. The treatment apparatus of claim 1, wherein the energy is RF energy.

11. A method of controlling a treatment apparatus including a handpiece, a tip module provided at an end of the handpiece, a driving unit disposed on an end portion of the handpiece, and a cooling unit, the method comprising steps of:
- operating the driving unit to advance micro needles so that a first part of each of the micro needles is inserted into a tissue;
- applying RF energy to the micro needles;
- driving the cooling unit after ending the applying of the RF energy and prior to retrieval of the micro needles; and
- retrieving the micro needles and positioning the micro needles at an original position,
- wherein the micro needles are provided on a substrate that reciprocates by a predetermined distance in the tip module,
- wherein the tip module includes an inner part in which the micro needles and the substrate are disposed and a wall sealing the inner part, the wall having at least one hole,
- wherein the driving unit includes an output terminal, and when operating the driving unit, the output terminal moves along the at least one hole and pressurizes the substrate,
- wherein the cooling unit includes a fan, and when driving the cooling unit, the fan supplies cooling air towards the inner part of the tip module through the at least one hole, thereby cooling all micro needles together,
- wherein a second part of each of the micro needles is protruded through the substrate in a specific length so that the second part of each of the micro needles is positioned opposite to the first part of each of the micro needles with respect to the substrate, the first part and the second part being included in a single body of each of the micro needles,
- wherein driving the cooling unit is performed to directly cool the second part of each of the micro needles protruded through the substrate without directly cooling a surface of the tissue,
- wherein the specific length is shorter than a length of the first part of each of the micro needles, and
- wherein the cooling unit is disposed between the driving unit and the wall of the tip module.

12. The method of claim 11, wherein:
- driving the cooling unit is performed until a temperature of the micro needles are cooled to a specific temperature or less, and
- the retrieving the micro needles is performed after the temperature of the micro needles drops to the specific temperature.

13. A method of a treatment of tissue, comprising:
- positioning a tip module on a surface of a tissue, the tip module provided at an end of a handpiece and comprising a plurality of micro needles;
- inserting a first part of each of the plurality of micro needles into the tissue by operating a driving unit disposed on an end portion of the handpiece;
- applying RF energy to the plurality of micro needles;
- cooling the tissue in contact with a side of the first part of each of the plurality of micro needles by directly cooling a second part of each of the plurality of micro needles using a cooling unit, without directly cooling the surface of the tissue, after ending the applying of the RF energy and prior to retrieval of the plurality of micro needles, the first part and the second part being included in a single body of each of the plurality of micro needles; and
- retrieving the first part of each of the plurality of micro needles from the tissue,
- wherein the second part of each of the plurality of micro needles is positioned opposite to the first part of each of the plurality of micro needles with respect to a substrate and has a specific length that is shorter than a length of the first part of each of the plurality of micro needles,
- wherein the tip module includes an inner part in which the plurality of micro needles and the substrate are disposed and a wall sealing the inner part, the wall having at least one hole, and
- wherein the driving unit includes an output terminal, and when operating the driving unit, the output terminal moves along the at least one hole and pressurizes the substrate,
- wherein the cooling unit includes a fan, and when cooling the tissue, the fan supplies cooling air towards the inner part of the tip module through the at least one hole, thereby cooling all micro needles together, and
- wherein the cooling unit is disposed between the driving unit and the wall of the tip module.

* * * * *